United States Patent [19]

Koskenniska et al.

[11] 4,265,824
[45] May 5, 1981

[54] PROCESS FOR THE ISOLATION OF β-SITOSTEROL CONTAINING A LOW PERCENTAGE OF α-SITOSTEROL

[75] Inventors: Lasse A. Koskenniska; Marie M. Puhakka, both of Oulu, Finland

[73] Assignee: Farmos-Yhtyma Oy, Turku, Finland

[21] Appl. No.: 100,502

[22] Filed: Dec. 5, 1979

[30] Foreign Application Priority Data

Dec. 12, 1978 [FI] Finland ................................ 783807

[51] Int. Cl.³ .............................................. C07J 9/00
[52] U.S. Cl. ............................................... 260/397.25
[58] Field of Search .................................... 260/397.25

[56] References Cited

U.S. PATENT DOCUMENTS 2,322,906  6/1943  Yoder ............................. 260/397.25
2,573,265  10/1951  Lange et al. ..................... 260/397.25
4,153,622  5/1979  Lamminkari et al. .......... 260/397.25

Primary Examiner—Elbert L. Roberts
Attorney, Agent, or Firm—McAulay, Fields, Fisher, Goldstein & Nissen

[57] ABSTRACT

A process for the isolation and recovery of β-sitosterol substantially free of α-sitosterol from the unsaponifiables obtained from crude soap skimmings or from a crude sterol mixture containing β-sitosterol, α-sitosterol and campesterol. The starting material is treated with an inorganic or organic acid in an organic solvent, whereby α-sitosterol reacts with the acid giving rearrangement products. The solution is cooled and filtered or the solvent is distilled off, whereafter the obtained crude β-sitosterol is recrystallized from an organic solvent, to yield the pure material.

6 Claims, No Drawings

PROCESS FOR THE ISOLATION OF β-SITOSTEROL CONTAINING A LOW PERCENTAGE OF α-SITOSTEROL

BACKGROUND OF THE INVENTION

This invention relates to a process for the isolation and recovery of β-sitosterol (I) substantially free from α-sitosterol (II).

The steroids in general form an important group of the modern drugs. One of these steroids is β-sitosterol, which is a lipotropic agent. β-sitosterol is even more important as a starting material in the production of other steroids. α-sitosterol is a harmful agent in the conversion of β-sitosterol to other steroid derivatives. It is therefor desirable to produce β-sitosterol free of α-sitosterol.

The present invention is a process for obtaining β-sitosterol which is substantially free of α-sitosterol from starting materials containing both α and β sitosterol, such as the unsaponifiable fraction obtained as a by-product of soap manufacturing from the crude soap skimmings of the sulfate pulp process using as raw material both pinewood and hardwood, especially birch. The β-sitosterol isolated according to the invention is pure enough for the use as starting material in the preparation of steroid intermediates as well as pharmaceutical β-sitosterol.

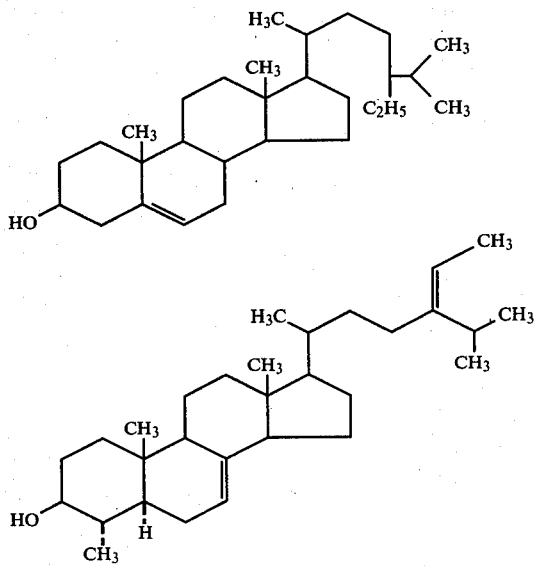

Although many processes for the separation of sterols from various sources are known, not many of these processes deal with the problems inherent in the separation of β-sitosterol from the neutral fraction obtained in the sulfate pulp processing of pinewood and hardwood. More particularly, prior processes were not generally concerned with obtaining β-sitosterol which is substantially free of α-sitosterol, from a mixture thereof.

U.S. Pat. No. 2,835,682, for example, concerns the recovery of sterols from sterol-containing materials in general. The method disclosed in this patent comprises fractionating a sterol containing mixture in a liquified, normally gaseous hydrocarbon, e.g. propane, to give a sterol-enriched fraction. The sterol-enriched fraction is then saponified in alcoholic alkali solution whereafter the sterols are crystallized by adding water, and cooling.

U.S. Pat. No. 2,866,797 shows the separation of sterols from unsaponifiables obtained from vegetable oils, tall oils, sugar cane oil and the like, by extraction and crystallization. The unsaponifiable fraction is extracted with ethylene dichloride, and small amounts of water and methanol are added to precipitate the sterols.

A more recent publication, U.S. Pat. No. 3,691,211, teaches a process for preparing sterols from plant sources, especially tall oil pitch, by extraction in a water-alcohol-hydrocarbon mixture, followed by saponification and subsequent recrystallization and leaching. The starting materials for this process are different than those contemplated for use in the present invention and the problems to be solved are different. Thus, although a good yield is obtained, it is not surprising that the process itself is not comparable to that of the present invention.

Another purification method is generally described in Chemical Abstracts, Vol. 81 (1974) 51409 v for purifying crude phytosterol derived from sulfate soap, to β-sitosterol. The process comprises dissolving in ligroin at 70°–75° C. and washing with water at 65°–70° C. The solution is then cooled to give 90.4 percent pure β-sitosterol, the yield being 69.5 percent.

The process disclosed in U.S. Pat. No. 4,044,031 is for the separation of sterols from e.g. the same neutral fraction as in the present invention. The process of U.S. Pat. No. 4,044,031 consists of dissolving the neutral fraction in a water-immiscible solvent, extracting the solution with a hydrophilic phase containing small amounts of water, and recovering sterols from the hydrophilic phase. This process, which utilizes extraction with two solvent phases, can be carried out continuously utilizing a counter-current extraction process.

As compared with all above mentioned processes, the process of the present invention is simpler and gives a better result. The present invention process successfully obtains β-sitosterol which is substantially free of α-sitosterol, and on a commercial scale.

No good process for the separation of α- and β-sitosterol is known. According to U.S. Pat. No. 2,573,265, steroids with a 3β-OH-group and a $C_{5-6}$ double bond, as for instance β-sitosterol, form acid addition products with $HCLO_4$ and $HPF_6$, which thereafter can be removed from the other neutral products. In the publication Sci.Res. (Dakka, Pak.) 1969, 162, the separation of α- and β-sitosterol chromatographically on aluminum oxide is described.

The present invention process is based on observations made during experiments with the purification of β-sitosterol. It was found, that α-sitosterol reacts much more easily with acids than β-sitosterol. By observing the reaction gas chromatographically and mass spectrometrically it was found, that α-sitosterol is rearranged in acid conditions so that the position of the double bond in the ring is changed, whereby many rearrangement products are formed, which have not been identified. If the acid treatment is continued for longer than the optimum time, the OH-group of α-sitosterol and at a later stage also the OH-group of β-sitosterol are split off to give dehydration products. In addition to this, a substitution of the OH-group with an acid rest, e.g. chlorine, occurs. The solubilities of both the rearrangement products and the dehydration products differ so much from the solubility of the sterol components that they are easily removed by crystallization. By suitable adjustment of the conditions only rearrangement products are obtained.

According to the book L. F. Fieser and M. Fieser, "Steroids," Reinhold Publishing Corp., New York 159, pages 113 and 114, $\Delta^{8(13)}$-ergostenol is isomerized in the presence of hydrogen chloride in chloroform to $\Delta^{14}$-ergostenol, and 5-hydroergosterol is isomerized under the same conditions to a mixture containing $\Delta^{8(14),22}$- and $\Delta^{14,22}$-ergostadienol. The reaction of $\alpha$- and $\beta$-sitosterol with acids has not, however, been studied before.

The rearrangement occurs only at the $C_{7-8}$ double bond of $\alpha$-sitosterol but not at the $C_{5-6}$ double bond of $\beta$-sitosterol. It is surprising that the reaction products can be removed from the mixture by a simple crystallization. Although rearrangements of this kind by steroids have been earlier described, it is surprising that the reaction can be utilized with such good result specifically for removing $\alpha$-sitosterol from $\beta$-sitosterol containing raw material.

BRIEF DESCRIPTION OF THE INVENTION

Briefly, the present invention process comprises treatment of the crude sterol mixture containing both $\alpha$- and $\beta$-sitosterol, with an acid. The reaction product is recovered by precipitation from the reaction mixture and the purified $\beta$-sitosterol recovered from the precipitate by crystallization from a suitable solvent.

DESCRIPTION OF PREFERRED EMBODIMENT

The process of the invention comprises the treatment of a crude sterol mixture containing $\beta$- and $\alpha$-sitosterol, with a strong inorganic or organic acid in an organic solvent. After the acid treatment the reaction product is recovered, e.g. by cooling the solution or evaporation of the solvent. Pure $\beta$-sitosterol may be obtained by crystallization from a suitable solvent.

Suitable starting materials include the unsaponifiables from a sulfate pulping process or crude $\beta$-sitosterol obtained from the unsaponifiables according to a process described in the U.S. Pat. No. 4,044,031. The unsaponifiable fraction usually contains over 10 percent of $\beta$-sitosterol. In addition betulin, betulaprenols, $\alpha$-sitosterol, campesterol and other neutral substances such as squalene, lignoseryl alcohol and behenyl alcohol and other similar constituents are normally present. The crude $\beta$-sitosterol contains $\beta$-sitosterol, $\alpha$-sitosterol and campesterol. It is particularly favorable and surprising that $\beta$-sitosterol free from $\alpha$-sitosterol can be obtained directly from the unsaponifiable fraction.

Acid treatment is preferably carried out using inorganic acids such as hydrogen chloride, hydrogen bromide and phosphoric acid. Organic acids such as methane sulfonic acid and p-toluenesulfonic acids are also suitable.

Suitable solvents are generally all organic solvents in which the sterol mixture or unsaponifiable fraction dissolve sufficiently. The best results have been obtained by using ethanol, isopropanol, acetone, toluene, xylene, and chloroform.

For carrying out the acid reaction, a temperature range of about 10°–150° C., and preferably about the boiling point of the mixture has been used.

For purification or recovery of $\beta$-sitosterol from the acid reaction products, suitable solvents are, for example, ethanol, isopropanol, chloroform, methylene chloride, toluene, ethyl acetate, acetone, heptane, methylethylketone, or their mixtures. Suitable solvent mixtures are e.g. ethanol-methylene chloride, heptane-methylene chloride and toluene-ethyl acetate.

When crude $\beta$-sitosterol is treated in the above mentioned way a crude product is obtained, which contains about 90 percent $\beta$-sitosterol, about 6 percent campesterol, rearrangement products and possibly dehydration products. When the conditions are suitably chosen, all of the $\beta$-sitosterol has reacted to form other products.

By crystallization from the above mentioned solvents the rearrangement and dehydration products are removed. Although the purified $\beta$-sitosterol contains campesterol, this is not objectionable for the use of $\beta$-sitosterol as starting material in the production of steroids.

When the unsaponifiable fraction starting material is boiled in organic solvents under acid conditions the rearrangement of $\beta$-sitosterol as discussed above, occurs. In addition to this the betulin, which is a cell poison, and the fatty acids in the unsaponifiable fraction decompose and these decomposition products are removed in the subsequent crystallization.

The purification process of the invention is thus a simple solution to an important problem. It can be accomplished on an industrial scale. When using the unsaponifiable fraction as starting material, not only is the harmful $\alpha$-sitosterol removed, but also removed is the poisonous betulin, which accompanies $\beta$-sitosterol in most purification processes.

The following examples illustrate the invention in more detail. In all examples, the crude $\beta$-sitosterol contains the following components: 59.4 percent $\beta$-sitosterol, 33.1 percent $\alpha$-sitosterol and 7.5 percent campesterol. The unsaponifiable fraction used in the examples contains 12.5 percent $\beta$-sitosterol, 25 percent betulaprenols, 10 percent $\alpha$-sitosterol, 7 percent campesterol and 10 percent betulin. Other suitable starting materials containing $\beta$-sitosterol and $\alpha$-sitosterol include tall oil pitch and neutral extracts derived from soya, wheat, sugar cane and other plant sources. The obtained products have been analysed gas chromatographically. In the examples 1–7 the $\alpha$-sitosterol has been completely removed.

A concentration of about 15–20% starting material in solvent (5 grams per 25 ml solvent) is used in the following examples as a preferred concentration for ease of handling small sample sizes. However, it has been found that a sample to solvent ratio range of 5 grams sample to between 5 and 100 milliliters solvent will give good results (about 5–50% starting material).

EXAMPLE 1

5.0 g of crude $\beta$-sitosterol and 25 ml of ethanol containing 2 percent gaseous hydrogen chloride, were added into a reaction flask. The mixture was refluxed and the reaction was followed with the gas chromatograph Varian 1400 (temperature of the oven 270° C., of the injection port 300° C. and of the detector 300° C. A 3 percent SE-30, chromosorb WHP, particle size 0.147–0.175 mm. length 3 m. column was used. The reaction was followed by gas chromatography, which indicated that after 3 hours refluxing, the $\alpha$-sitosterol had reacted.

The mixture was cooled and the precipitate filtered. 3.3 g of product (66 percent) was obtained, which contained 90.0 percent $\beta$-sitosterol, 6.4 percent campesterol and 3.6 percent rearrangement products, which were removed by crystallizing the product from 15 ml of ethanol. 3 g (60 percent) of product was then obtained containing 93.6 percent β-sitosterol and 6.4 percent campesterol. The melting point of the product was 136°–138° C.

EXAMPLE 2

To the reaction flask was added 5.0 g of crude β-sitosterol, 25 ml of chloroform and about 0.1 percent by weight of the solution of hydrogen chloride gas. The solution was refluxed for 6 hours. The mixture was cooled, which gave 2.8 g of product. This contained 92 percent β-sitosterol, 6.3 percent campesterol and 1.7 percent of rearrangement products. The precipitate was crystallized from 10 ml of isopropanol giving 2.4 g product, which contained 93.7% β-sitosterol and 6.3 percent campesterol. The melting point was 137°–138° C.

EXAMPLE 3

5.0 g of crude β-sitosterol was weighed into a reaction flask and 25 ml of toluene and about 0.1 percent gaseous hydrogen chloride was added. The solution was refluxed for 4 hours. The toluene was evaporated, 20 ml of ethanol was added, the mixture was cooled and the precipitate filtered. 2.8 g (56 percent) of product was obtained containing 90.1 percent β-sitosterol, 6.4 percent campesterol and 3.5 percent rearrangement products.

EXAMPLE 4

To a reaction flask was added 5.0 g of crude β-sitosterol, 25 ml of ethanol and 1 ml of 40 percent HBr in glacial acetic acid. The mixture was boiled for 6 hours. The solution was cooled and the precipitate filtered. 2.5 g (50 percent) of product was obtained, which contained 93.0 percent β-sitosterol, 6.4 percent campesterol and 0.4 percent rearrangement products.

EXAMPLE 5

5.0 g of the unsaponifiable fraction obtained from crude soap skimmings was weighed in a reaction flask and 25 ml of ethanol containing 5 percent hydrogen chloride was added. The mixture was refluxed for 6 hours and the solution cooled below +5° C. The products precipitated as white crystals. The yield was 0.5 g (10.0 percent) of a product containing 88.0 percent β-sitosterol, 5.8 percent campesterol and 6.2 percent rearrangement products, which could be removed by crystallization as in example 1.

EXAMPLE 6

5.0 g of the unsaponifiable fraction was weighed and 25 ml of ethanol and 1 ml of 40 percent HBr in glacial acetic acid was added. The mixture was refluxed for 10 hours. The solution was cooled and the precipitate filtered. 0.5 g (10 percent) of product was obtained. It contained 88.0 percent β-sitosterol, 5.7 percent campesterol and 6.3 percent rearrangement products.

EXAMPLE 7

5.0 g crude β-sitosterol was weighed into a reaction flask. 25 ml of chloroform was added and the temperature of the mixture was adjusted to +10° C. and 0.2 g of hydrogen chloride gas was added. The mixture was kept for 24 hours at +10° C. and then cooled to 0° C. The precipitate was filtered, giving 2.9 g of a product, which contained 93.0 percent β-sitosterol, 6.4 percent campesterol and 0.6 percent rearrangement products. The melting point of the product was 137°–138° C.

The examples 8–36 are set forth in table 1.

TABLE 1

| Ex. No. | Starting material 5 grams | Solvent | ml | Acid | Concentration of acid % | Reaction time hours | Yield grams | Yield % | β-sitosterol | campesterol | α-sitosterol | rearrangement products |
|---|---|---|---|---|---|---|---|---|---|---|---|---|
| 8 | crude β-sitosterol | chloroform | 25 | HCl | c. 0.5 | 6 | 2.8 | 56.0 | 92.0 | 6.3 | — | 1.7 |
| 9 | crude β-sitosterol | isopropanol | 25 | HCl | 5.0 | 2 | 2.6 | 52.0 | 92.4 | 6.4 | — | 1.2 |
| 10 | crude β-sitosterol | isopropanol | 25 | HCl | 1.0 | 15 | 3.3 | 66.0 | 78.0 | 6.4 | 10.2 | 5.4 |
| 11 | crude β-sitosterol | toluene | 25 | HCl | c. 0.5 | 4 | 2.8 | 56.0 | 90.1 | 6.4 | — | 3.5 |
| 12 | crude β-sitosterol | xylene | 25 | HCl | c. 0.5 | 12 | 3.0 | 60.0 | 88.0 | 6.4 | — | 5.5 |
| 13 | crude β-sitosterol | ethanol | 25 | HCl | 1 | 6 | 4.0 | 80.0 | 76.0 | 6.3 | 14.0 | 3.7 |
| 14 | crude β-sitosterol | ethanol | 25 | HCl | 0.5 | 16 | 4.1 | 82.0 | 74.0 | 6.4 | 14.6 | 5.0 |
| 15 | crude β-sitosterol | ethanol | 25 | HCl | 2.0 | 3 | 3.2 | 64.0 | 91.0 | 6.4 | — | 2.6 |
| 16 | crude β-sitosterol | ethanol | 25 | HCl | 5.0 | 2 | 2.8 | 56.0 | 93.0 | 6.5 | — | 0.5 |
| 17 | crude β-sitosterol | ethanol | 25 | HCl | 1.0 | 8 | 3.3 | 66.0 | 90.0 | 6.4 | — | 3.6 |
| 18 | crude β-sitosterol | ethanol | 25 | HCl | 2.0 | 2 | 3.3 | 66.0 | 89.0 | 6.5 | — | 4.5 |
| 19 | crude β-sitosterol | ethanol | 25 | HBr/CH₃COOH | 2 | 6 | 2.5 | 50.0 | 93.0 | 6.4 | — | 0.4 |
| 20 | crude β-sitosterol | ethanol | 25 | HBr/CH₃COOH | 10 | 2 | 2.8 | 56.0 | 90.5 | 6.2 | — | 3.6 |
| 21 | crude β-sitosterol | isopropanol | 25 | HBr/CH₃COOH | 2 | 16 | 3.0 | 60.0 | 88.0 | 6.3 | 0.4 | 5.3 |
| 22 | crude β-sitosterol | chloroform | 25 | HBr/CH₃COOH | 2 | 2 | 2.8 | 56.0 | 90.2 | 6.4 | — | 3.6 |
| 23 | crude β-sitosterol | ethanol | 25 | H₃PO₄ | 0.1 | 10 | 3.0 | 60.0 | 88.0 | 6.4 | 1.2 | 4.4 |
| 24 | crude β-sitosterol | ethanol | 25 | CH₃SO₃H | 0.5 | 16 | 3.2 | 64.0 | 86.0 | 6.5 | 2.4 | 5.1 |
| 25 | unsaponifiable fraction from crude soap skimmings | ethanol | 25 | HCl | 5 | 2 | 0.5 | 10.0 | 87.0 | 5.8 | 1.2 | 6.0 |
| 26 | unsaponifiable fraction from crude soap skimmings | ethanol | 25 | HCl | 5 | 6 | 0.5 | 10.0 | 88.0 | 5.8 | — | 0.2 |
| 27 | unsaponifiable fraction from crude soap skimmings | ethanol | 25 | HBr/CH₃COOH | 2 | 10 | 0.5 | 10.0 | 88.0 | 5.7 | — | 6.3 |
| 28 | unsaponifiable fraction from crude soap skimmings | ethanol | 25 | CH₃SO₃H | 1 | 8 | 0.45 | 9.0 | 87.0 | 5.8 | 1.6 | 5.6 |
| 29 | unsaponifiable fraction from crude soap skimmings | ethanol | 25 | HCl | 2 | 8 | 0.6 | 12.0 | 92.0 | 6.2 | — | 1.8 |
| 30 | unsaponifiable fraction from crude soap skimmings | isopropanol | 25 | HCl | 2 | 6 | 0.5 | 10.0 | 91.5 | 6.1 | — | 2.4 |
| 31 | from crude soap skimmings | chloroform | 25 | HCl | c. 1 | 3 | 0.55 | 11.0 | 93.0 | 6.2 | — | 0.8 |

TABLE 1-continued

| Ex. No. | Starting material 5 grams | Solvent | ml | Acid | Concentration of acid % | Reaction time hours | Yield grams | Yield % | β-sitosterol | campesterol | α-sitosterol | rearrangement products |
|---|---|---|---|---|---|---|---|---|---|---|---|---|
| 32 | unsaponifiable fraction from crude soap skimmings | isopropanol | 25 | HCl | 5 | 2 | 0.6 | 12.0 | 92.5 | 6.1 | — | 1.4 |
| 33 | unsaponifiable fraction from crude soap skimmings | chloroform | 25 | HBr/CH$_3$COOH | 1 | 2 | 0.55 | 11.0 | 91.0 | 6.2 | — | 2.8 |
| 34 | unsaponifiable fraction from crude soap skimmings | ethanol | 25 | p-CH$_3$C$_6$H$_4$SO$_3$H | 4 | 5 | 0.50 | 10.0 | 89.0 | 6.0 | 2.0 | 3.0 |
| 35 | unsaponifiable fraction from crude soap skimmings | acetone | 25 | HBr/water | 4 | 6 | 0.40 | 8.0 | 88.0 | 6.2 | 2.1 | 3.7 |
| 36 | unsaponifiable fraction from crude soap skimmings | toluene | 25 | HBr/CH$_3$COOH | 2 | 6 | 0.45 | 9.0 | 90.5 | 6.1 | 1.0 | 2.4 |
| 37 | crude β-sitosterol | ethanol 100 | | HCl 0.5 | 4 | 1.5 | 30.0 | 93.0 | 93.0 | 6.0 | — | 1.0 |
| 38 | crude β-sitosterol | ethanol | 50 | HCl | 0.5 | 4 | 2.6 | 52.0 | 92.3 | 6.0 | — | 1.7 |
| 39 | crude β-sitosterol | ethanol | 5 | HCl | 25 | 6 | 4.0 | 80.0 | 76.0 | 6.3 | 3.7 | 14.0 |

What is claimed is:

1. A process for the isolation of β-sitosterol which is substantially free of α-sitosterol, from a material comprising a mixture of α- and β-sitosterol, comprising:
   (a) dissolving said mixture in a first organic solvent selected from the class consisting of ethanol, acetone, isopropanol, toluene, xylene, chloroform, and mixtures thereof;
   (b) reacting the solution of (a) with a strong acid selected from the class consisting of hydrogen chloride, hydrogen bromide, phosphoric acid, methanesulfonic acid, and p-toluenesulfonic acid, to form a crude reaction product;
   (c) recovering the reaction products from (b) from said first organic solvent;
   (d) dissolving the reaction products of (c) in a second organic solvent selected from the class consisting of ethanol, isopropanol, chloroform, methylene chloride, toluene, ethylacetate, acetone, heptane, methylethylketone, and mixtures thereof; and thereafter
   (e) selectively crystallizing β-sitosterol from said second solvent.

2. The process of claim 1 wherein said acid is added in an amount of from about 0.05 to about 15 percent by weight of the mixture.

3. The process of claim 2 wherein the recovery of reaction products from the first solvent is accomplished by cooling the first solvent to cause the reaction products to crystalize out, and thereafter filtering the reaction products from the first solvent.

4. The process of claim 2 wherein the recovery of reaction products from the first solvent is accomplished by evaporating the first solvent to leave the reaction products as a residue.

5. The process of claim 2 wherein said reaction mixture comprises approximately 15%–20% by weight of starting material.

6. The process of claim 2 wherein said starting material comprises unsaponifiable of crude soap skimmings.

* * * * *

UNITED STATES PATENT AND TRADEMARK OFFICE
CERTIFICATE OF CORRECTION

PATENT NO. : 4,265,824
DATED : May 5, 1981
INVENTOR(S) : Lasse A. Koskenniska and Marie M. Puhakka It is certified that error appears in the above—identified patent and that said Letters Patent is hereby corrected as shown below:

Column 4, line 8 "β-sitosterol" should be --α-sitosterol-- line 17 "β-sitosterol" should be --α-sitosterol--

Signed and Sealed this

Third Day of November 1981

[SEAL]

*Attest:*

GERALD J. MOSSINGHOFF

*Attesting Officer*     *Commissioner of Patents and Trademarks*